United States Patent

Nambu et al.

[11] Patent Number: 5,163,425
[45] Date of Patent: Nov. 17, 1992

[54] DEFORMABLE CAP FOR SCALP COOLING

[76] Inventors: Masao Nambu, 447-17, Honmoku Motomachi, Naka-ku, Yokohama; Masaru Fuji, 26-9, Hamakazecho, Ashiya, Hyogo; Yoko Motizuki, 4-22-1-305, Nishikamata, Oota-ku, Tokyo; Takashi Tsujino, 2-23-7, Narusedai, Machida, Tokyo, all of Japan

[21] Appl. No.: 158,122

[22] Filed: Feb. 16, 1988

Related U.S. Application Data

[63] Continuation of Ser. No. 865,123, May 20, 1986, abandoned.

[30] Foreign Application Priority Data

May 27, 1985 [JP] Japan ............... 60-77743[U]
May 27, 1985 [JP] Japan ............... 60-77744[U]

[51] Int. Cl.⁵ ............................... A61F 7/10
[52] U.S. Cl. ............................ 128/380; 128/402; 128/403
[58] Field of Search ............. 128/379, 380, 381, 399, 128/400, 401, 402, 403; 446/219, 220

[56] References Cited

U.S. PATENT DOCUMENTS

| 683,991 | 10/1901 | Rowe | 128/402 |
|---|---|---|---|
| 743,473 | 11/1903 | Evax | 128/403 |
| 1,002,021 | 8/1911 | Barnes | 128/402 |
| 1,127,221 | 2/1915 | Finkelstein | 128/402 |
| 1,169,123 | 1/1916 | Burns | 128/402 |
| 1,511,775 | 10/1924 | Rioux et al. | 128/402 |
| 1,535,448 | 4/1925 | Boord | 128/402 |
| 1,603,001 | 10/1926 | Carter | 128/402 |
| 1,769,186 | 7/1930 | Morris | 128/402 |
| 2,031,197 | 2/1936 | Weaver | 128/402 |
| 2,049,723 | 8/1936 | Pomeranz | 128/402 |
| 2,320,467 | 6/1943 | Rabil | 128/402 |
| 2,547,886 | 4/1951 | Poux | 128/402 |
| 3,463,161 | 8/1969 | Andrassy | 128/402 |
| 3,545,230 | 12/1970 | Morse | 128/403 |
| 3,587,577 | 6/1971 | Smirnov et al. | 128/402 |
| 3,980,300 | 9/1976 | Hornsby, Jr. | 446/219 |
| 3,988,568 | 10/1976 | Mantell | 128/380 |
| 4,003,572 | 1/1977 | Harvey | 446/220 |
| 4,147,921 | 4/1979 | Walter et al. | 128/380 |
| 4,356,709 | 11/1982 | Alexander | 128/402 |
| 4,404,820 | 9/1983 | Romaine | 128/399 |
| 4,462,224 | 7/1984 | Dunshee et al. | 128/403 |
| 4,530,220 | 7/1985 | Nambri et al. | 128/403 |
| 4,596,250 | 6/1986 | Beisang, III et al. | 128/403 |

*Primary Examiner*—Michael Safavi

[57] ABSTRACT

A deformable cap for scalp cooling is provided. The cap contains a cap member obtained by discharging air inside a hollow ball made of flexible material and a plurality of small pieces of high water content hydrogel contained in the cap member. The hydrogel is prepared by casting an aqueous solution of polyvinyl alcohol into a mold, cooling the cast aqueous solution to −10° C. or lower to obtain a cooled frozen mass followed either by thawing the cooled frozen mass and one to seven additional cooling and thawing operations or by partially dehydrating the cooled frozen mass in vacuum.

10 Claims, 1 Drawing Sheet

DEFORMABLE CAP FOR SCALP COOLING

This application is a continuation of application Ser. No. 865,123, filed on May 20, 1986, now abandoned.

BACKGROUND OF THE INVENTION

1. Field of the Invention

This invention relates to a cap for scalp cooling or scalp hypothermia and more particularly to a cap for scalp cooling which can be deformed into intimate contact with the scalp.

2. Related Art Statement

A variety of gel compositions have hitherto been proposed to be used as cooling media and some of them are applied for practical uses. Such a gel is referred to as a cooling gel, chilling gel, coldness-keeping gel, coldness-keeping heat transfer medium, colloidal coolant, coldness-keeping means, coolant composition or Icenon (Trade Name), i.e. ice pillow. Some of these coldness-keeping means are specifically designed for scalp cooling. However, these scalp cooling means are inconvenient in that, since they are of a predetermined size and shape, they cannot be intimately contacted with the scalp area in its entirety and in that they cannot be deformed freely so that while they can be applied to some users, they cannot be applied to other users.

When filler materials such as chilled water, ice water, viscous solutions or fluid flaccid gels are charged into a hollow pouch which then is applied to the head to cool the scalp area in its entirety, the filler materials unnecessarily tend to descend to lie in uneven distribution so that it is difficult to maintain the desired shape of the pouch even with the use of bands or the like fasteners.

OBJECTS AND SUMMARY OF THE INVENTION

It is a principal object of the present invention to provide a deformable cap for scalp cooling that can be easily attached and detached and that can be adapted to contact intimately with the total ares of the head of various shape and dimensions.

It is another object of the present invention to provide a deformable cap for scalp cooling for preventing alopecia induced as a secondary effect of administration of antitumor antibiotics.

The above and other objects of the invention will become apparent from the following description.

According to the invention, there is provided a deformable cap for scalp cooling comprising:

a cap member obtained by discharging air inside a hollow ball made of flexible material; and a plurality of small pieces of hydrogel having high water content and sealingly contained in-between walls forming the cap, the hydrogel being prepared by a process comprising a casting step of casting an aqueous solution or suspension containing more than 8 wt. % and not more than 25 wt. % of a polyvinyl alcohol having a degree of hydrolysis of not less than 98 mol% and an average polymerization degree of not less than 1000 into a mold having a desired shape and dimensions, a freezing step of cooling the cast aqueous solution or suspension to a temperature of not higher than −(minus) 10° C. to obtain a cooled frozen mass, a thawing step of thawing the cooled frozen mass, and one to seven additional cyclic processing steps each including the freezing and thawing steps.

According to the invention, there is also provided a deformable cap for scalp cooling comprising:

a cap member obtained by discharging air inside a hollow ball made of flexible material; and a plurality of small pieces of hydrogel having high water content and sealingly contained between walls forming the cap, the hydrogel being prepared by a process comprising a casting step of casting an aqueous solution or suspension containing more than 8 wt. % and not more than 25 wt. % of a polyvinyl alcohol having a degree of hydrolysis of not less than 98 mol% and an average polymerization degree of not less than 1000 into a mold having desired shape and dimemsions, a freezing step of cooling the cast aqueous solution or suspension to a temperature of not higher than −(minus) 10° C. to obtain a cooled frozen mass, and a partial dehydration step of dehydrating the cooled frozen mass in vacuum until the percentage dehydration rate reaches a value not less than 3 wt. %.

DESCRIPTION OF THE INVENTION

Figure 3:
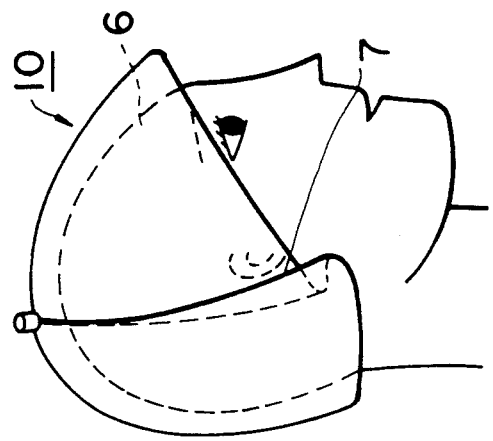
FIG. 3 is a diagrammatic view showing the deformable cap attached to the head.

The present invention will be explained in further detail.

The polyvinyl alcohol used in the present invention should have a degree of hydrolysis of not less than 98 mol% and preferably not less than 98.5 mol%. With use of the polyvinyl alcohol having the degree of hydrolysis in the range of 80 to 88 mol% and, above all, not higher than 85 mol%, only a flaccid gel is obtained instead of a desired rubber-like resilient member. Also the polyvinyl alcohol should have a polymerization degree of not less than 1,000, otherwise the produced gel tends to be inferior in mechanical strength. It is therefore preferred to use the polyvinyl alcohol with the polymerization degree in the range of 1,000 to 3,300, for example, the usually marketed type of the polyvinyl alcohol with the polymerization degree of 1,000 to 2,600.

According to the present invention, an aqueous solution or an aqueous suspension, hereafter referred to comprehensively as aqueous solution, containing the aforememtioned polyvinyl alcohol, is prepared. The concentration of polyvinyl alcohol in the solution should be within the range of more than 8 wt. % and not more than 25 wt. %, preferably from 9 to 15 wt. %. Although the concentration can be higher than 25 wt. %, the viscosity of the aqueous solution is then increased drastically, thus inconveniencing the operation. In addition, the water contents are lower than 75 wt. % while the coldness-keeping properties are diminished. With the concentration lower than 8 wt. %, the molded hydrogel tends to collapse while being too flaccid to be used as cooling medium.

When the deformable cap for scalp cooling obtained in accordance with the present invention is not cooled previously to a temperature below the freezing point but simply to be cooled to for example 0° to 10° C., it is only sufficient if the aqueous solution of the polyvinyl alcohol is prepared in the manner described above. However, when the cap for scalp cooling should be used after it is previously cooled to not higher than 0° C., the freezing point of the hydrogel can be lowered to a temperature of not higher than 0° C., for example, to −15° C. to −20° C.

In these cases, water-soluble organic compounds as anti-freezing or freezing point decreasing agent is dissolved in the aforementioned aqueous solution of polyvinyl alcohol prior to formation of the hydrogel. The water-soluble organic compounds may include water-soluble monohydric alcohols such as methyl alcohol, ethyl alcohol or isopropyl alcohol or derivatives thereof; water-soluble polyhydric alcohols such as ethylene glycol, propylene glycol, 1, 3-propylene glycol, glycerol or 2-methyl-2,4-pentanediol; and other water-soluble organic compounds such as acetone, dimethylsulfoxide, methylsulfonic acid, ethylsulfonic acid, dimethylamine, methylamine or formic acid. There may also be used monosaccharides such as erithritol, arabinose, xylose, xylitol, glucose, glucitol (sorbitol or sorbite), gluconic acid, glucuronic acid, glucaric acid, galacturonic acid, fructose, or glucosamine; disaccharides such as sucrose, cellobiose or lactose; trisaccharides such as raffinose; or water-soluble polysaccharides such as agarose, amylose, sodium alginate, glycogen, chondroitin, chondroitin sulfate, dextran, pectinic acid, alginic acid propylene glycol ester, tragacanth gum, pullulan or chondroitin sodium sulfate. Amongst these compounds, ethylene glycol, propylene glycol, glycerol and D-sorbitol are most preferred in consideration of contribution thereof to the mechanical strength of the resulting hydrogel, achievement of the target of freezing point decrease by substitution of a relatively small amount and the merit of odorlessness and extremely low volatility.

The concentration of the aforementioned water-soluble organic solvents which may be present may preferably be in the range from 5 to 40 wt. % and preferably 10 to 35 wt. %. If the concentration of the compounds present together is higher than 40 wt. %, the freezing point may be unnecessarily lowered or elevated thus causing economic demerits. By the co-existence of the water-soluble organic compounds, the freezing temperature of the hydrogel becomes lower than −20° C. so that the hydrogel is not frozen at the temperature of −10° to −20° C. in the ice chamber of the domestic refrigerator for maintaining its flaccidity and the touch similar to that of the living tissue.

When preparing an aqueous solution containing both the polyvinyl alcohol and the water-soluble organic compound or compounds, a variety of methods can be used, such as the method of admixing, dissolving or suspending both of the polyvinyl alcohol and the water-soluble organic compounds in water, the method of previously dissolving polyvinyl alcohol in water and then admixing the water-soluble organic compounds or aqueous solutions thereof into the resulting solution or the method of admixing, dissolving or suspending polyvinyl alcohol powders or aqueous solutions of polyvinyl alcohol into water-soluble organic compounds or aqueous solutions thereof. In any of these methods, the concentration of the polyvinyl alcohol is adjusted to be more than 8 wt. % and not more than 25 wt. % while that of the water-soluble organic compounds is in the range of 5 to 40 wt. %.

According to the present invention, an aqueous solution or aqueous suspension containing polyvinyl alcohol alone or as a combination with the water-soluble organic compounds is cast into a desired casting mold and molded on cooling.

For such cooling, freezing mixtures such as 23:77 mixture of table salt and ice (−21° C.) or 30–70 mixture of calcium chloride and ice (−55° C.), dry ice-methyl alcohol (−72° C.) or liquid nitrogen (−196° C.) may be used for cooling to a temperature not higher than −10° C. While cooling to a temperature of −269° C. is feasible with the use of liquid helium, it is not only uneconomical but has no merits on the quality of the hydrogel. Therefore, it suffices to use a Freon refrigerator for cooling to, for example, −20° to −80° C. It goes without saying that the hydrogel be stored in the ice making chamber of the domestic refrigerator or freezer. Insufficient cooling is not desirable according to the present invention since the mechanical properties of the resulting gel is thereby lowered. Therefore, according to the invention, an aqueous solution containing polyvinyl alcohol either singly or in combination with the water-soluble organic compound or compounds is cooled to the temperature not higher than −10° C. and preferably not higher than −20° C.

According to the present invention, after termination of the aforementioned cooling or freezing operation, and the resulting frozen mass is thawed, in such a manner that a series of freezing and thawing steps are consecutively performed with the number of the additional freezing and thawing steps being 1 to 7, for producing a high water content hydrogel to be used in the present invention. With increase in the number of times of cumulative freezing and thawing steps, the resulting high water content hydrogel is improved in hardness, however, the effect of incrementing the number of the freezing and thawing steps is drastically lowered for the number of the additional freezing and thawing steps of not less than 8 (see Polymer Application, written by Masao Nambu, 32, 523(1983)). Therefore, the number of the additional cycles is 1 to 7 and preferably 2 to 5.

According to the present invention, the aforementioned freezing and thawing steps may be dispensed with and the frozen mass obtained by cooling to a temperature not higher than −10° C. may be subjected to a partial dehydration step in vacuum. The mechanical strength of the hydrogel is improved with increase in the rate of dehydration (reduction percentage in weight of the frozen mass). However, if the usage as the coldness-keeping hydrogel is considered, it is not necessary to markedly elevate the dehydration rate for obtaining the hydrogel with improved strength. Rather it is preferred that the rate of dehydration be not less than 3 wt. % and not less than 3.5 wt. % in view of flaccidity and elasticity of the hydrogel. The dehydration in vacuum means dehydrating in vacuum. Although no limitations are placed on the extent of pressure reduction, it may for instance be not higher than 1 mmHg and preferably not higher than 0.1 mmHg and more preferably not higher than 0.08 mmHg.

According to the present invention, the thus-obtained high water content hydrogel is formed into small pieces. As an alternative, an aqueous solution containing the polyvinyl alcohol alone or in combination with the water-soluble organic compound may be cast into molds adapted for forming the small pieces for directly forming a plurality of high water content small pieces. Any desired shape of the small pieces of the high water content hydrogel such as cubes, parallelepipeds, columns or spheres may be employed. The size of the small pieces of the high water content hydrogel is also not critical, it being only necessary that the piece may be freely deformed upon application of the finger pressure from the outer surface. The preferred size of the side or diameter is usually 2 mm to 3 cm.

Figure 1:
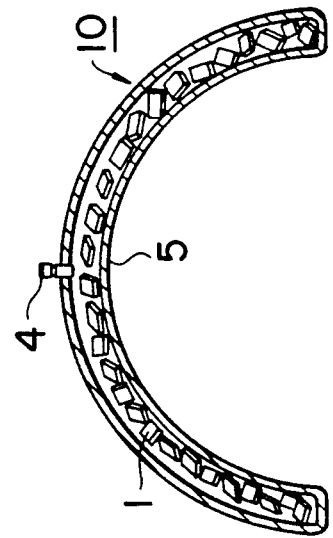
FIG. 1 is a perspective view partially cut away and showing small pieces of high water content hydrogel accommodated within the hollow ball for the preparation of the deformable cap for scalp cooling according to the present invention.

A preferred embodiment of the deformable cap for scalp cooling is explained by referring to the accompanying drawing. Referring to FIG. 1, small pieces 1 of the high water content hydrogel or high water content rubber obtained in the manner as described above are enclosed in a hollow ball 2 of spherical or elliptical shape of resilient material.

Figure 2:
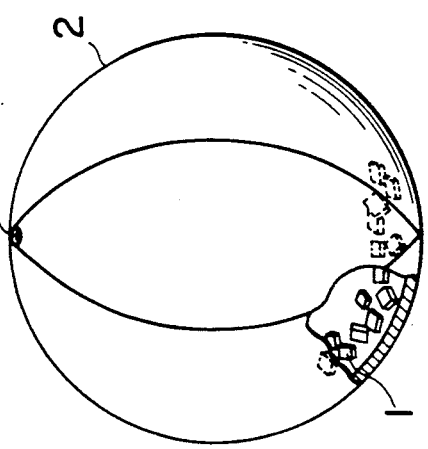
FIG. 2 is a sectional view showing the cap for scalp cooling of the invention, obtained upon air exhaustion.

More than 0.3 kg of the small pieces 1 are preferably enclosed in the ball 2 in view of the required coldness-keeping properties. In view of the load on the patient wearing the coldness-keeping cap, the object of preventing alopecia can be sufficiently achieved by not higher than 3 kg, preferably 0.3 to 3 kg and more preferably 0.35 to 2 kg. The flexible hollow ball 2 containing the small pieces of the hydrogel 1 are preferably rubber balls of reduced wall thickness or hollow balls of plastic films such as polyvinyl chloride, polyethylene or polypropyrene in view of touch on the scalp and sealing properties. For example, beach balls of PVC, balloons of polypropylene-nylon composite film or rubber balls of reduced film thickness may be conveniently used. Rugby balls or balls for American football games, airships or model toys of UFO's can be used insofar as they are provided with the function of the spherical or elliptical hollow ball of the present invention. When the small pieces of the hydrogel or water-containing rubber are enclosed in one of these hollow balls, an injection port 3 can be formed through the wall surface of the hollow ball. Alternatively, the port 3 can be previously formed at the time of the manufacture of the hollow ball 2. According to the present invention, a predetermined amount of the small pieces of the water-containing rubber are injected into the port 3, after which the redundant air is discharged out from the inside of the hollow ball 2. That is, for obtaining the recess on the ball wall surface to be used as cap or head cover, it is necessary that air be discharged from the interior of the hollow ball. If air discharging is insufficient and a large amount of air remains in the interior of the hollow ball, the small pieces 1 tend to flow down to obstruct uniform cooling of the overall area of scalp. In this manner, the discharging of air has an extremely important significance. However, it is not always necessary to expel the total air from the inside of the ball, it being only necessary that most of the air be discharged by pressuring the ball wall surface. Then, the port 3 on the ball wall surface is closed and sealed completely. For this sealing, the port 3 can be heat-sealed or bound with a string or the port can be stopped with a plug. Alternatively, the port 3 may have its fringe bonded together with an adhesive. FIG. 2 shows the cap obtained upon discharging the air from the inside of the ball. In the present example, the port 3 is sealed by a sealing plug 4.

The cap 10 for cooling the scalp is now obtained by the above described air discharging and ball wall sealing operation with the hollow ball necessarily presenting the crescent shape, such as ship or boat shape.

The amount of admixture of the high water content rubber or hydrogel may be in the range from 0.3 to 3 kg, as mentioned hereinabove. With the thickness of the admixed hydrogel pieces higher than 3 cm, the duration of coldness-keeping period is unnecessarily protracted, while an excess weight load is imposed on the user. Therefore, it is preferred that the amount of filling of the high water content hydrogel be selected in dependence upon the size of the hollow ball so that the thickness of the pieces may be in the range from 0.6 to 2.5 cm and preferably from 0.8 to 2 cm. Preferred examples of the charging or filling are 1.2 to 2 kg for the hollow ball 32 cm in diameter, with the thickness of the pieces of hydrogel being 0.8 to 2 cm, and 0.3 to 0.6 kg for the hollow ball 16 cm in diameter, with the thickness of the pieces of hydrogel also being 0.8 to 2 cm.

When attaching the deformable cap 10 of the present invention on the user's head, with the inner recessed portion of the cap applied to the head 6, finger pressure is applied from the outer surface of the cap for shifting certain portion or portions of the filled small pieces of hydrogel so that the total scalp areas will be covered substantially uniformly by the small pieces of hydrogel, while the shape of the cap is ultimately adjusted to suit the shape of the user's head so that the cap is intimately contacted with the total scalp area as by nipping any excess portion of the cap wall for suitably reducing the size of the cap or providing one or more folds or creases in any excess portion lying beyond the head perimeter.

Figure 4:
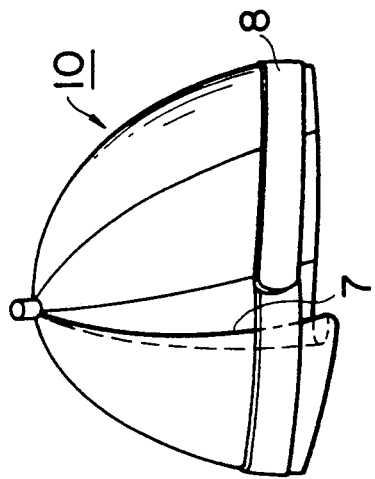
FIG. 4 is a diagrammatic view showing a flat fastener wrapped about the cap.

According to the present invention, resilient belts 8 such as bands, flat fasteners or elastomeric bandages may be preferably wrapped about and secured to the cap skirt for maintaining intimate contact of the attached cap to the head skin even on the occasion of the to-and-fro movements of the user's head ( see FIG. 4 ).

Regarding the size of the hollow ball, the following points need be considered for intimately contacting and covering the total area of the scalp. Since the head shape of the infants, boys and girls is nearly spherical, substantially all area of the head skin can be covered by the semi-circular coldness-keeping cap with the diameter equivalent to the head perimeter. The eyebrows nuchal region and side-whiskers can also be cooled by using a coldness-keeping cap having a size larger than the perimeter of the head. In this case, any excess ball wall portion of the cap lying outside of the perimeter is folded and resilient bands 8 such as flat fastener or "Velcro" fastener (Trade Mark), which is a material having a surface with projecting fibers for releasably engaging projecting fibers on another surface, or elastomeric bandages are placed about the skirt portion of the cap so as to lie in intimate contact with the perimeter of the cap 10. In the case of adults, while the size of the skull lying above the height of the eyes is not so different from that of the infants, the vertical length of the face and head is longer than that of the infants. It is therefore preferred to make use of the vertically elongated or ellipsoidal coldness-keeping cap. However, as an alternative measure, a spherical ball with a size larger than the size of the perimeter of the skull is used and any excess portion or portions of the ball wall is nipped or creased (FIG. 3, numeral 7). As described above, an elastic belt or band 8 may be wrapped around the skirt of the cap to reduce the ball diameter to trim the ball to a vertically long pot-like shape. Therefore, for covering the scalp in its entirety, the spherical shape of the ball with the diameter of 15 to 32 cm or the ellipsoidal shape of the ball with the long diameter of 15 to 32 cm and the short diameter of 12 to 32 cm is preferred. Above all, with the infants with the head perimeter of 33.5 to 51 cm, the spherical shape with the diameter of 15 to 24 cm, the ellipsoidal shape with the short diameter of 12 to 24 cm and the long diameter of 15 to 24 cm are preferred. For boys and girls with the head perimeter of 50 to 52 cm, the spherical shape with the diameter of 17 to 25 cm and the ellipsoidal shape with the short diameter of 14 to 25 cm and the long diameter of 17 to 25 cm are preferred. For adults, the spherical shape with the diameter of 19 to 32 cm or the ellipsoidal shape with the short diameter of 17 to 32 cm and the long diameter of 19 to 32 cm are preferred. With these hollow balls, not only the scalp but also desired portions of the head such as rear and temporal regions or eyebrows can be covered. In addition, sideburns, side-whiskers or huchal regions can be covered if so desired.

According to the present invention, the overall area of the scalp can be covered by the filler of the small pieces of the high water content hydrogel. In addition, by suitably displacing the filler upon application of the finger pressure, the cap can be deformed to the desired shape as a function of the head shape of the user. The desired shape can be maintained after releasing the finger pressure.

The deformable cap of the present invention can be suitably employed for inhibiting alopecia caused upon administration of antitumor antibiotics to the patients suffering from cancer. Above all, it is advantageously employed for preventing and inhibiting severe alopecia occurring as the secondary effect of administration of Adriamycin, that is, 14-hydroxy daunorubicin or doxorubicin.

For using the deformable cap for scalp cooling of the present invention in the usual form, it is stored overnight in the refrigerator maintained at 3° to 10° C. Then, before injecting Adriamycin, the cap is applied to the head in the manner as described above so that the small pieces of hydrogel contained in the cap are intimately contacted with and adapted to the scalp area.

With the thickness of 13 mm of the small pieces of hygrogel filled, for example, the temperature of the head skin is maintained at not higher than 25° C. for 30 minutes and at not higher than 30° C. for 60 minutes. Usually, the aim of preventing alopecia is sufficiently fulfilled by cooling the scalp temperature to 25° to 30° C. for 15 minutes after injection.

Usually, the time necessary for Adriamycin injection is less than about 5 minutes. In some hospitals, however, it is administered by intravenous drip infusion continuing for one to two hours. In the latter case, the coldness-keeping time duration can be extended by using the thickness of hydrogel pieces filled in the cap which is increased to 2.5 to 3.5 cm. However, in view of the increased weight load to the user, the cap may be substituted by the previously cooled new cap at intervals of 30 to 60 minutes during the drip infusion periods, with the thickness of the hydrogel pieces filled being 0.8 to 2 cm as described above.

Adriamycin is usually administered in an amount of 30 to 50 mg/m$^2$ which is the amount of administration per 1 m$^2$ of body surface area. There have also been instances wherein larger amounts such as 60 to 80 mg/m$^2$ which is 1.6 to 2.3 mg/kg for adults, 1.6 to 2.5 mg/kg for 13 to 19 age group, 2 to 3.5 mg/kg for 7 to 12 age group and 2.5 to 11 mg/kg for 0 to 6 age group. For such massive administration, there is also a demand for deep cooling (J. G. Dean, S. E. Salmon et al., N.Eng. J.Med., 301,253 (1977)). For meeting this demand, the hydrogel or rubber obtained by simultaneously using the aforementioned water-soluble organic compound or compounds is filled to a thickness of 2 to 3 cm, and the resulting cap is stored in a freezing chamber of $-20°$ C. of a freezer for pre-cooling and the thus cooled cap is applied to the user. In this manner, the scalp temperature may be maintained at a temperature not higher than 20° C. for 40 to 50 minutes after application thereof to the user.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A deformable ball for use in forming a cap member for cooling a patient's skull, which comprises: an inflated ball of flexible material; sealable port means in said ball for introducing small pieces of a cooling substance into said ball; sealable venting means for removing air from said ball, said ball being dimensioned so that when deformed to the shape of a cap, the cap fits about the patient's skull and contains the pieces of cooling substance around its periphery; and a band for wrapping the cap about and intimately securing the cap to the skull.

2. The deformable ball according to claim 1, wherein the port means and venting means are the same.

3. The deformable ball of claim 1, wherein the cooling substance is a high water-content hydrogel.

4. A method of forming a cooling cap over the skull of a patient in need thereof, which comprises: injecting pieces of a cooling substance into a deformable ball through a port means; removing air from the ball through venting means to form a cap; positioning the pieces of cooling substance around the periphery of the cap; and sealing the port and venting means.

5. A method according to claim 4 wherein 0.3 to 3 kg of small pieces of high water content hydrogel are accommodated within the cap.

6. A method according to claim 4 wherein each of the pieces of said cooling substance has a diameter of 2 mm to 3 cm.

7. A method according to claim 4 further including the step of wrapping a band about the cap and intimately securing the cap to the skull.

8. The method of claim 4 wherein the port means and venting means are the same.

9. The method of claim 4 ,wherein the cooling substance is a high water-content hydrogel.

10. The method of claim 4, wherein the cooling substance consists of small pieces of high water content hydrogel filler and wherein the cap is deformed to the shape of the patient's skull by finger pressure on the filler pieces.

* * * * *

UNITED STATES PATENT AND TRADEMARK OFFICE
CERTIFICATE OF CORRECTION

PATENT NO. : 5,163,425
DATED : November 17, 1992
INVENTOR(S) : NAMBU et al.

It is certified that error appears in the above-identified patent and that said Letters Patent is hereby corrected as shown below:

On the cover page insert: -- Assignee: Sumitomo Rubber Industries, Ltd.
Hyogo-Ken, Japan and
Nippon Oil Co., Ltd.
Tokyo, Japan On the cover page insert: Attorney, Agent, or Firm - Keil & Weinkauf Signed and Sealed this Ninth Day of November, 1993

Attest:

BRUCE LEHMAN

Attesting Officer

Commissioner of Patents and Trademarks